United States Patent [19]

Atsumi et al.

[11] 4,410,696
[45] Oct. 18, 1983

[54] ANTITUMOR AND IMMUNOSUPPRESSIVE 4-CARBAMOYLIMIDAZOLIUM-5-OLATE DERIVATIVES

[75] Inventors: Toshio Atsumi, Kawanishi; Tetsutaro Sanjiki, Ibaraki; Takao Kiyohara, Takarazuka, all of Japan

[73] Assignee: Sumitomo Chemical Company, Limited, Osaka, Japan

[21] Appl. No.: 305,347

[22] Filed: Sep. 24, 1981

[51] Int. Cl.³ .......................................... C07D 233/90
[52] U.S. Cl. .................................. 542/427; 548/337; 424/273 R
[58] Field of Search ...................... 542/427; 424/273 R

[56] References Cited

U.S. PATENT DOCUMENTS 4,317,825  3/1982  Atsumi et al. ........................ 548/336
4,332,806  6/1982  Atsumi et al. .................. 424/273 R

FOREIGN PATENT DOCUMENTS 24172  2/1981  European Pat. Off. .

OTHER PUBLICATIONS

Sumitomo, *Chemical Abstracts*, vol. 96, (1982), No. 122795r.

*Primary Examiner*—Robert W. Ramsuer
*Attorney, Agent, or Firm*—Wenderoth, Lind & Ponack

[57] ABSTRACT

There are provided compounds of the formula:

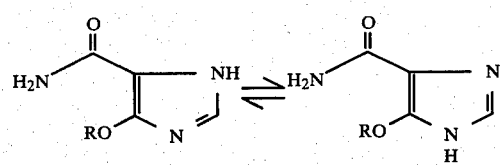

wherein R is a mono-substituted benzoyl group wherein the substituent is a phenyl group, an alkanoyl group, a formyl group, a halogeno-alkyl group, an aralkyloxy group, a phenoxy group, an alkoxycarbonyl group, an aralkyloxycarbonyl group, an alkanoyloxy group, a benzoyl group, a carboxyl group, a hydroxy group, a group of the formula:

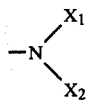

(wherein $X_1$ and $X_2$ are a hydrogen atom or a lower alkyl group), an aralkyloxycarbonylamino group, a lower alkoxycarbonylamino group, a carboxyamino group or a carbamoyl group; a cinnamoyl group which may be substituted at the α position or the phenyl ring with an alkyl group, an alkoxy group, an aryl group, a nitro group, a methylenedioxy group, a formyl group, a halogeno-alkyl group, a halogen atom, a hydroxy group, a carboxyl group, an amino group or a cyano group; or a benzoyl group substituted with from two to five of the same or different substituents selected from the group consisting of alkyl groups, alkoxy groups, aralkyloxy groups, nitro group, halogen atoms, hydroxy group, alkanoyloxy groups, formyl group, carboxyl group, alkylthio groups, alkylsulfonyl groups, groups of the formula:

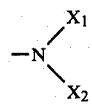

(wherein $X_1$ and $X_2$ are a hydrogen atom or a lower alkyl group), sulfo group and sulfamoyl group; or its non-toxic salt, and a process for producing them. The compounds are useful as antitumor agents and immunosuppressants.

11 Claims, No Drawings

ANTITUMOR AND IMMUNOSUPPRESSIVE 4-CARBAMOYLIMIDAZOLIUM-5-OLATE DERIVATIVES

The present invention relates to novel 4-carbamoylimidazolium-5-olate derivatives and a process for preparing them. More particularly, the present invention pertains to 4-carbamoylimidazolium-5-olate derivatives useful as antitumor agents and immunosuppressants, a pharmaceutical composition containing at least one of them, and a process for preparing them.

The novel imidazole derivatives of the present invention are those represented by the following formula (I)

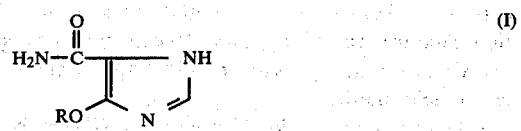

wherein R is a mono-substituted benzoyl group wherein the substituent is a phenyl group, an alkanoyl group, a formyl group, a halogeno-alkyl group, an aralkyloxy group, a phenoxy group, an alkoxycarbonyl group, an aralkyloxycarbonyl group, an alkanoyloxy group, a benzoyl group, a carboxyl group, a hydroxy group, a group of the formula:

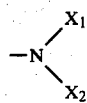

(wherein $X_1$ and $X_2$ are a hydrogen atom or lower alkyl group), an aralkyloxycarbonylamino group, a lower alkoxycarbonylamino group, a carboxyamino group or a carbamoyl group; a cinnamoyl group which may be substituted at the α position or the phenyl ring with an alkyl group, an alkoxy group, an aryl group, a nitro group, a methylenedioxy group, a formyl group, a halogeno-alkyl group, a halogen atom, a hydroxy group, a carboxyl group, an amino group or a cyano group; or a benzoyl group substituted with from two to five of the same or different substituents selected from the group consisting of alkyl groups, alkoxy groups, aralkyloxy groups, nitro group, halogen atoms, hydroxy group, alkanoyloxy groups, formyl group, carboxyl group, alkylthio groups, alkylsulfonyl groups, groups of the formula:

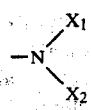

(wherein $X_1$ and $X_2$ are a hydrogen atom or a lower alkyl group), sulfo group and sulfamoyl group, or its non-toxic salt.

As used herein, the term "alkanoyl" means lower alkanoyl having 2 to 6 carbon atoms (e.g. acetyl, propionyl, pivaloyl hexanoyl), medium alkanoyl having 7 to 12 carbon atoms (e.g. octanoyl, lauroyl) and higher alkanoyl having 13 to 22 carbon atoms (e.g. palmitoyl).

The term "halogeno-alkyl" means lower alkyl having 1 to 6 carbon atoms substituted with a halogen atom as later defined (e.g. trifluoromethyl, β-chloroethyl).

The term "aralkyloxy" means lower alkoxy having 1 to 6 carbon atoms substituted with an aryl group such as benzyloxy, α-methylbenzyloxy, phenethyloxy and the like.

The term "alkoxycarbonyl" means lower alkoxy carbonyl having 2 to 7 carbon atoms (e.g. methoxycarbonyl, ethoxycarbonyl, n-propoxycarbonyl, isopropoxycarbonyl), medium alkoxycarbonyl having 8 to 13 carbon atoms (e.g. octyloxycarbonyl) and higher alkoxycarbonyl having 14 to 23 carbon atoms (e.g. octadecyloxycarbonyl, docosyloxycarbonyl).

The term "aralkyloxycarbonyl" means a carbonyl substituted with the above aralkyloxy group (e.g. benzyloxycarbonyl, α-methylbenzyloxycarbonyl, phenethyloxycarbonyl and the like).

The term "alkanoyloxy" means lower alkanoyloxy having 2 to 6 carbon atoms (e.g. acetoxy, propionyloxy, pivaloyloxy, hexanoyloxy), medium alkanoyloxy having 7 to 12 carbon atoms (e.g. octanoyloxy, lauroyloxy) and higher alkanoyloxy having 13 to 22 carbon atoms (e.g. palmitoyloxy, stearoyloxy).

The term "aralkyloxycarbonylamino" means an amino group substituted with the above aralkyloxycarbonyl group.

The term "lower alkoxycarbonylamino" means an amino group substituted with the above lower alkoxycarbonyl group.

The term "alkyl" means lower alkyl having 1 to 6 carbon atoms (e.g. methyl, ethyl, n-propyl, iso-propyl, n-butyl, isobutyl, t-butyl, hexyl), medium alkyl having 7 to 12 carbon atoms (e.g. octyl, decyl, dodecyl) and higher alkyl having 13 to 22 carbon atoms (e.g. pentadecyl, docosyl).

The term "alkoxy" means lower alkoxy having 1 to 6 carbon atoms (e.g. methoxy, ethoxy, n-propoxy, isopropoxy, n-butoxy, isobutoxy), medium alkoxy having 7 to 12 carbon atoms (e.g. octyloxy, dodecyloxy) and higher alkoxy having 13 to 22 carbon atoms (e.g. octadecyloxy, docosyloxy).

The term "aryl" means such groups as phenyl, tolyl, naphthyl and the like.

The term "halogen" means fluorine, chlorine, bromine and iodine.

The term "alkylthio" means thio substituted with the above alkyl group.

The term "alkylsulfonyl" means sulfonyl substituted with the above alkyl group.

The term "lower alkyl" in $X_1$ or $X_2$ means a lower alkyl having 1 to 6 carbon atoms as stated above.

The term "cinnamoyl" means cinnamoyl unsubstituted or substituted at the α position or the phenyl ring with one or more of the same or different substituents selected from the groups as described, such as p-methylcinnamoyl, p-methoxycinnamoyl, α-phenylcinnamoyl, m-nitrocinnamoyl, 3,4-methylenedioxycinnamoyl, p-formylcinnamoyl, m-trifluoromethylcinnamoyl, p-chlorocinnamoyl, p-aminocinnamoyl, p-hydroxycinnamoyl, o-carboxycinnamoyl, α-methylcinnamoyl, α-fluorocinnamoyl, α-cyano-p-hydroxycinnamoyl, 2,6-dichlorocinnamoyl, 2,5-dimethoxycinnamoyl, 3,4-dimethylcinnamoyl, 4-hydroxy-3-methoxycinnamoyl, 3,4-dihydroxycinnamoyl, 2,4,5-trimethoxycinnamoyl, 3,5-dimethoxy-4-hydroxycinnamoyl and the like.

The compound of the formula (I) of the present invention can be prepared by reacting 4-carbamoylimidazolium-5-olate (II)

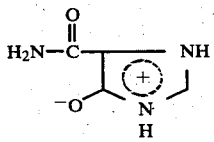

or its reactive derivative with a carboxylic acid of the formula (III);

R—OH                                                   (III)

wherein R is as defined above or its reactive derivative.

Examples of preferred reactive derivatives of carboyllic acids of the formula (III) are carboxylic acid halides (e.g. chlorides, bromides, iodides, fluorides), carboxylic acid anhydrides, mixed anhydrides (e.g. mixed anhydrides with ethyl chloroformate, isobutyl chloroformate and the like), activated esters (e.g. p-nitrophenyl ester, ester with N-hydroxysuccinimide), imidazolide (e.g. prepared by reacting N,N'-carbonyldiimidazole with a carboxylic acid (III)), activated intermediates prepared by reacting a carboxylic acid (III) with reaction products obtained from N,N-dimethylformamide and oxalyl chloride (or phosgene or thionyl chloride or phosphorus pentachloride) and the like.

Examples of preferred reactive derivatives of 4-carbamoylimidazolium-5-olate of the formula (II) are trimethylsilyl derivatives, trialkyltin derivatives, mercury salts, silver salts and the like.

Typical examples of preferred solvents which may be used in this reaction are methylene chloride, chloroform, pyridine, diethyl ether, tetrahydrofuran, dioxane, benzene, toluene, methanol, ethanol, N,N-dimethylformamide, formamide, N,N-dimethylacetamide, acetonitrile, nitromethane, acetone, ethyl acetate, dimethylsulfoxide, dichloromethane, dichloroethane, xylene and water.

The reaction can generally be effected at a reaction temperature from $-78°$ to $100°$ C. preferably from $-60°$ to $60°$ C.

The reaction of 4-carbamoylimidazolium-5-olate with said carboxylic acid halides can usually be carried out in an inert polar solvent or a mixture of water and inert organic solvent, preferably in the presence of an inorganic or organic base, at a temperature from $-10°$ to $60°$ C. using one to two mole equivalents of the acid halide.

Typical examples of said inert polar solvent are tetrahydrofuran, dioxane, pyridine, N,N-dimethylformamide, formamide, N,N-dimethylacetamide and dimethylsulfoxide. Typical examples of said inert organic solvents are tetrahydrofuran, dioxane, diethyl ether, chloroform, dichloromethane, dichloroethane, benzene, toluene, and xylene. Examples of preferred inorganic base are sodium hydroxide, sodium carbonate, sodium bicarbonate, potassium carbonate or bicarbonate and potassium hydroxide. Examples of preferred organic base are pyridine, triethylamine and N,N-dimethylaniline.

The reaction of 4-carbamoylimidazolium-5-olate with the activated intermediate prepared by reacting a carboxylic acid (III) with reaction products obtained from N,N-dimethylformamide and oxalyl chloride (or phosgene or thionyl chloride or phosphorus pentachloride) can usually be carried out in an organic solvent (e.g. acetonitrile, pyridine, N,N-dimethylformamide, N,N-dimethylacetamide, chloroform) at a temperature from $-78°$ to $80°$ C.

The compounds of the formula (I) can also be prepared by reacting a silylated derivative of 4-carbamoylimidazolium-5-olate with reactive derivatives of a carboxylic acid (III) (e.g. acid halides) at a temperature from $-78°$ to $50°$ C. in an inert organic solvent (e.g. dimethylformamide, tetrahydrofuran, dioxane, diethyl ether, benzene, toluene).

The silylated derivatives of 4-carbamoylimidazolium-5-olate are known and can be prepared by known methods (Hayashi, et al. Japanese Patent Publication (Kokai) No. 50-121276). When the compounds of the formula (I) exist in the form of their silylated derivative in the reaction mixture, the compound (I) can be obtained by disilylation reaction with desilylating reagents (e.g. acetic acid, methanol).

When the reactive derivative of acid (III) is the acid halide, the eliminated halide can be neutralized by an organic base (e.g. triethylamine, pyridine).

The compounds of the formula (I) substituted with an amino, hydroxy and carboxyl group can be prepared by the said acylation methods after protecting the amino, hydroxy and carboxyl group with protective groups (e.g. benzyl, benzyloxycarbonyl, t-butoxycarbonyl and the like) and then removing the protective groups.

The compounds of the formula (I) can be isolated and purified by known purification methods (e.g. recrystalization, column chromatography).

The compounds of the formula (I) may form a salt with an inorganic acid (e.g. hydrochloric acid, sulfuric acid, nitric acid, phosphoric acid) or an organic acid (e.g. p-toluenesulfonic acid, benzenesulfonic acid, methanesulfonic acid, tartaric acid, malic acid, lactic acid, maleic acid, fumaric acid).

The imidazole derivatives of the present invention may exist in a mixture of the two tautomers as follows:

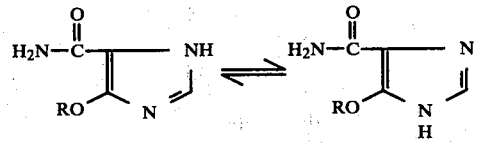

both of which are within the scope of the present invention.

The compounds of the present invention possess potent antitumor activities against Sarcoma 180, Lewis lung carcinoma, Ehrlich carcinoma, P-388 leukemia and the like. The compounds of the formula (I) are useful as antitumor agents, and they exhibit particularly excellent inhibitory effects against tumors and also exhibit a prolonging effect on the life span.

The antitumor activities of the compounds of the present invention were estimated according to the methods described in "Cancer Chemotherapy Reports" Part 3, Vol. 3, (No. 2) p. 13 (1972). The results are given in the following Table 1.

TABLE 1
Antitumor effect on mouse experimental tumors

| Compound | Dose (mg/kg) Route i.p. | Schedule | Inhibition Ratio (%) Lewis lung carcinoma (solid) |
|---|---|---|---|
| 5-Carbamoyl-1H—imidazole-4-yl p-phenylbenzoate | 100 | 5q2d | 77.0 |
| 5-Carbamoyl-1H—imidazole-4-yl p-chlorocinnamate | 100 | 5q2d | 90 |
| 5-Carbamoyl-1H—imidazole-4-yl m-nitrocinnamate | 100 | 5q2d | 90 |
| 5-Carbamoyl-1H—imidazole-4-yl 3',4'-dimethoxybenzoate | 100 | 5q2d | 83.1 |
| 5-Carbamoyl-1H—imidazole-4-yl 3'-methoxy-4'-methylbenzoate | 100 | 5q2d | 89.4 |

BDF$_1$ male mice, 5 weeks old, weighing between 18 and 22 grams were used. Each test group was composed of 6 to 7 mice. Two million cells of Lewis Lung carcinoma were injected in the hind leg. The drug was administered intraperitoneally at day 1, 3, 5, 7 and 9 (or 5q2d).

After killing the mice at day 13, tumors were removed and weighed. The tumor inhibitory ratio was calculated according to the following formula.

$$\text{Inhibition Ratio} = \left(1 - \frac{\text{the mean tumor weights of treated group}}{\text{the mean tumor weights of control group}}\right) \times 100$$

The compounds of the present invention also possess excellent immunosuppressive activity as well as potent antitumor activity.

The compounds (I) of the present invention have low toxicity. They do not show any toxic symptoms even when over 1000 mg/kg of the compounds are orally administered to a mouse. Moreover, they do not exhibit the influence of decreasing peripheral leucocytes, which is one of the most serious side effects of immunosuppressants.

The compounds of the present invention can be administered orally or parenterally to a warm-blood animal at a daily dose of 2–200 mg/kg as an antitumor agent, and 1–100 mg/kg as an immunosuppressant agent, in a conventional dosage unit form.

The compounds of the present invention may be made up alone or together with a conventional pharmaceutical carrier or diluent into a conventional solid or liquid pharmaceutical preparation (e.g. powders, granules, tablets, capsules, suspensions, emulsions, solutions) using the conventional methods in the pharmaceutical field. For example, tablets or capsules may contain 50–500 mg of the compounds (I).

Especially, the compounds (I) of the present invention can be used for oral administration and are effective for a long period.

The following examples are given to illustrate the present invention more precisely but it is not intended to limit the present invention thereto.

EXAMPLE 1

To a suspension of 0.636 g. of 4-carbamoylimidazolium-5-olate in 15 ml of dry pyridine was dropwise added 1.2 g of 2,6-dimethylbenzoyl chloride at a temperature below 5° C. in N$_2$ atmosphere. After being stirred for two hours at 41°–43° C., the reaction mixture was cooled to room temperature and 0.8 g of triethylamine was added, and separated crystals were filtered off. Then the filtrate was concentrated under reduced pressure, and separated crystals were filtered off, washed with toluene and ether and dried to give 0.689 g of 5-carbamoyl-1H-imidazole-4-yl 2',6'-dimethylbenzoate, m.p. 176°–177° C.

Crude material was recrystallized from N,N-dimethylformamide and water. m.p.: 180°–180.5° C.

$\nu_{max}^{nujol}$ (cm$^{-1}$): 3425, 3160, 1725, 1670, 1610

| Elemental analysis: | C (%) | H (%) | N (%) |
|---|---|---|---|
| Calculated for C$_{13}$H$_{13}$N$_3$O$_3$·0.3H$_2$O | 59.00 | 5.18 | 15.88 |
| Found | 59.1 | 5.0 | 15.6 |

EXAMPLE 2

Following a procedure similar to that of Example 1 but using 0.636 g of 4-carbamoylimidazolium-5-olate and 1.30 g of 3,4-dimethoxybenzoyl chloride there was obtained 1.353 g of 5-carbamoyl-1H-imidazole-4-yl 3',4'-dimethoxybenzoate. m.p.: 209.5° C. (dec.)

Crude material was recrystallized from N,N-dimethylformamide and water. m.p.: 216.5° C.

$\nu_{max}^{nujol}$ (cm$^{-1}$): 3440, 3330, 3120, 1750, 1650, 1590

| Elemental analysis: | C (%) | H (%) | N (%) |
|---|---|---|---|
| Calculated for C$_{13}$H$_{13}$N$_3$O$_5$ | 53.61 | 4.50 | 14.43 |
| Found | 53.38 | 4.43 | 14.30 |

EXAMPLE 3

Following a procedure similar to that of Example 1 but using 0.636 g of 4-carbamoylimidazolium-5-olate and 2.0 g of 2,4,6-trimethoxybenzoyl chloride there was obtained 0.699 g of 5-carbamoyl-1H-imidazole-4-yl 2',4',6'-trimethoxybenzoate. m.p.: 174° C. (charred)

Crude material was recrystallized from N,N-dimethylformamide and water. m.p.: 184.5° C. (charred)

$\nu_{max}^{nujol}$ (cm$^{-1}$): 3410, 3330, 1750, 1670, 1610, 1590

| Elemental analysis: | C (%) | H (%) | N (%) |
|---|---|---|---|
| Calculated for C$_{14}$H$_{15}$N$_3$O$_6$ | 52.34 | 4.71 | 13.08 |
| Found | 52.2 | 4.8 | 13.2 |

EXAMPLE 4

Following a procedure similar to that of Example 1 but using 0.508 g of 4-carbamoylimidazolium-5-olate and 1.83 g of 3,4-bisbenzyloxybenzoyl chloride there was obtained 1.548 g of 5-carbamoyl-1H-imidazole-4yl 3',4'-bisbenzyloxybenzoate. m.p.: 189.5°–191.5° C.

Crude material was recrystallized from N,N-dimethylformamide and water. m.p.: 191.5°–192.5° C.

$\nu_{max}^{nujol}$ (cm$^{-1}$): 3460, 3150, 1740, 1670, 1605

| Elemental analysis: | C (%) | H (%) | N (%) |
|---|---|---|---|
| Calculated for C$_{25}$H$_{21}$O$_5$N$_3$ | 67.71 | 4.77 | 9.48 |
| Found | 67.4 | 4.9 | 9.3 |

EXAMPLE 5

A suspension of 0.55 g of 5-carbamoyl-1H-imidazole-4-yl 3',4'-bisbenzyloxybenzoate and 0.3 g of 10% Pd-C in dry tetrahydrofuran was stirred for 6 hours at room temperature in $H_2$ atmosphere. Separated precipitates were filtered off and the filtrate was concentrated under reduced pressure to give 0.270 g of 5-carbamoyl-1H-imidazole-4-yl 3',4'-dihydroxybenzoate. m.p.: 156° C.

Crude material was recrystallized from dimethylsulfoxide and water. m.p.: 159°-161° C.

$\nu_{max}^{nujol}$ (cm$^{-1}$): 3480, 3225, 1735, 1675, 1600

| Elemental analysis: | C (%) | H (%) | N (%) |
|---|---|---|---|
| Calculated for $C_{11}H_9N_3O_5.1.2H_2O$ | 46.39 | 4.03 | 14.75 |
| Found | 46.46 | 3.81 | 14.45 |

EXAMPLE 6

A mixture of 0.212 g of 3,5-dinitrobenzoic acid, 0.127 g of 4-carbamoylimidazolium-5-olate and 0.206 g of dicyclohexylcarbodiimide in 4 ml of dry pyridine was stirred for 21 hours at room temperature. Separated precipitates were filtered off and were washed with ethyl acetate to give 0.355 g of 5-carbamoyl-1H-imidazole-4-yl 3',5'-dinitrobenzoate which was recrystallized from dimethylsulfoxide and water. m.p.: 220° C. (decomp.)

| Elemental analysis: | C (%) | H (%) | N (%) |
|---|---|---|---|
| Calculated for $C_{11}H_7N_5O_7$ | 41.13 | 2.20 | 21.81 |
| Found | 41.5 | 2.4 | 20.9 |

EXAMPLE 7

Following a procedure similar to that of Example 6 but using 0.83 g of 3-methoxy-4-methylbenzoic acid, 1.03 g of dicyclohexylcarbodiimide and 0.635 g of 4-carbamoylimidazolium-5-olate there was obtained 1.45 g of 5-carbamoyl-1H-imidazole-4-yl 3'-methoxy-4'-methylbenzoate.

Crude material was recrystallized from N,N-dimethylformamide and water. m.p.: 210° C. (decomp.)

$\nu_{max}^{nujol}$ (cm$^{-1}$): 3450, 1740, 1655, 1600

EXAMPLE 8

A mixture of 76.26 g of 4-carbamoylimidazolium-5-olate, 174.31 g of 1,1,1,3,3,3-hexamethyldisilazane, 1.59 g of ammonium sulfate and 500 g of dry xylene was refluxed for 4 hours. The reaction mixture was concentrated under reduced pressure and a tris-trimethylsilylated derivative of 4-carabamoylimidazolium-5-olate was obtained. m.p.: 83°-86.5° C.

To a stirred solution of 1.718 g of tris-trimethylsilylated derivative of 4-carbamoyl-imidazolium-5-olate in 15 ml of dry tetrahydrofuran was dropwise added a solution of 0.833 g of cinnamoyl chloride in 5 ml of dry tetrahydrofuran at −50° C. under $N_2$ atmosphere. After being stirred for half an hour at −50° C., 0.32 g of dry methanol was added to the reaction mixture. After being stirred for 15 minutes at −50° C., 0.51 g of triethylamine was added.

The reaction mixture was heated up to room temperature and then separated crystals were filtered off, washed with tetrahydrofuran and chloroform and dried to give 0.796 g of 5-carbamoyl-1H-imidazole-4-yl cinnamate. m.p.: 170°-175° C. The filtrate of a tetrahydrofuran solution was concentrated and diethylether was added to the residue and separated crystals were filtered off, washed with diethyl ether and dried to give 0.427 g of said product.

Crude material was recrystallized from dimethylsulfoxide and water. m.p.: 197° C. (charred)

$\nu_{max}^{nujol}$ (cm$^{-1}$): 3460, 3160, 3110, 1720, 1670, 1605

| Elemental analysis: | C (%) | H (%) | N (%) |
|---|---|---|---|
| Calculated for $C_{13}H_{11}N_3O_3.0.1H_2O$ | 60.27 | 4.36 | 16.22 |
| Found | 60.1 | 4.4 | 16.3 |

EXAMPLE 9

Following a procedure similar to that of Example 8 but using 0.9 g of p-methylcinnamoyl chloride there was obtained 1.270 g of 5-carbamoyl-1H-imidazole-4-yl p-methylcinnamate. m.p.: 171° C. (decomp.)

Crude material was recrystallized from dimethylsulfoxide and water. m.p.: 194° C. (charred)

$\nu_{max}^{nujol}$ (cm$^{-1}$): 3440, 3150, 1715, 1665, 1600

| Elemental analysis: | C (%) | H (%) | N (%) |
|---|---|---|---|
| Calculated for $C_{14}H_{13}N_3O_3.0.2H_2O$ | 61.17 | 4.91 | 15.29 |
| Found | 61.19 | 4.69 | 15.49 |

EXAMPLE 10

Following a procedure similar to that of Example 8 but using 1.01 g of p-chlorocinnamoyl chloride there was obtained 1.408 g of 5-carbamoyl-1H-imidazole-4-yl p-chlorocinnamate. m.p. 172° C. (dec.)

Crude material was recrystallized from dimethylsulfoxide and water. m.p.: 202° C. (dec.)

$\nu_{max}^{nujol}$ (cm$^{-1}$): 3440, 3380, 3150, 1725, 1660, 1615

| Elemental analysis: | C (%) | H (%) | N (%) |
|---|---|---|---|
| Calculated for $C_{13}H_{10}N_3O_3Cl.0.1H_2O$ | 53.20 | 3.5 | 14.32 |
| Found | 53.1 | 3.8 | 14.1 |

EXAMPLE 11

Following a procedure similar to that of Example 8 but using 1.053 g of 3,4-methylenedioxycinnamoyl chloride there was obtained 1.172 g of 5-carbamoyl-1H-imidazole-4-yl 3',4'-methylenedioxycinnamate. m.p.: 165°-175° C.

Crude material was recrystallized from dimethylsulfoxide and water. m.p.: 189° C. (char.)

$\nu max^{nujol}$ (cm$^{-1}$): 3460, 3400, 3125, 1735, 1670, 1630, 1605

| Elemental analysis: | C (%) | H (%) | N (%) |
|---|---|---|---|
| Calculated for $C_{14}H_{11}N_3O_5.0.4H_2O$ | 54.51 | 3.86 | 13.62 |
| Found | 54.49 | 3.71 | 13.48 |

EXAMPLE 12

Following a procedure similar to that of Example 8 but using 0.98 g of p-methoxycinnamoyl chloride, there was obtained 1.15 g of 5-carbamoyl-1H-imidazole-4-yl p-methoxycinnamate. m.p.: 165°-167° C. (dec.)

Crude material was recrystallized from dimethylsulfoxide and water. m.p.: 185° C. (char.)
$v_{max}^{nujol}$ (cm$^{-1}$): 3470, 3175, 1725, 1670, 1605.

| Elemental analysis: | C (%) | H (%) | N (%) |
| --- | --- | --- | --- |
| Calculated for C$_{14}$H$_{13}$N$_3$O$_4$.0.6H$_2$O | 56.41 | 4.80 | 14.10 |
| Found | 56.75 | 4.63 | 13.85 |

EXAMPLE 13

Following a procedure similar to that of Example 8 but using 0.97 g of p-formylcinnamoyl chloride, there was obtained 1.086 g of 5-carbamoyl-1H-imidazole-4-yl p-formylcinnamate.

Crude material was recrystallized from dimethylsulfoxide and water. m.p.: 233° C. (char.)
$v_{max}^{nujol}$ (cm$^{-1}$): 3100, 1730, 1680, 1650, 1620, 1590

| Elemental analysis: | C (%) | H (%) | N (%) |
| --- | --- | --- | --- |
| Calculated for C$_{14}$H$_{11}$N$_3$O$_4$.0.5H$_2$O | 57.14 | 4.11 | 14.28 |
| Found | 57.0 | 3.9 | 14.0 |

EXAMPLE 14

Following a procedure similar to that of Example 8 but using 1.173 g of m-trifluoromethylcinnamoyl chloride, there was obtained 1.236 g of 5-carbamoyl-1H-imidazole-4-yl m-trifluoromethylcinnamate. m.p.: 167°–170° C. (dec.)

Crude material was recrystallized from dimethylsulfoxide and water. m.p.: 188° C. (char.)
$v_{max}^{nujol}$ (cm$^{-1}$): 3460, 3175, 1730, 1680, 1610

| Elemental analysis: | C (%) | H (%) | N (%) |
| --- | --- | --- | --- |
| Calculated for C$_{14}$H$_{10}$N$_3$O$_3$F$_3$.0.1H$_2$O | 51.42 | 3.14 | 12.85 |
| Found | 51.19 | 2.98 | 13.09 |

EXAMPLE 15

Following a procedure similar to that of Example 8 but using 1.058 g of m-nitrocinnamoyl chloride, there was obtained 1.383 g of 5-carbamoyl-1H-imidazole-4-yl m-nitrocinnamate.

Crude material was recrystallized from dimethylsulfoxide and water. m.p.: 197° C. (char.)
$v_{max}^{nujol}$ (cm$^{-1}$): 3450, 3120, 1740, 1650, 1600

| Elemental analysis: | C (%) | H (%) | N (%) |
| --- | --- | --- | --- |
| Calculated for C$_{13}$H$_{10}$N$_4$O$_5$.0.3H$_2$O | 50.75 | 3.47 | 18.21 |
| Found | 50.76 | 3.30 | 18.20 |

EXAMPLE 16

Following a procedure similar to that of Example 1 but using 1.46 g of α-phenylcinnamoyl chloride, there was obtained 1.186 g of 5-carbamoyl-1H-imidazole-4-yl α-phenylcinnamate. m.p.: 208° C.

Crude material was recrystallized from dimethylsulfoxide and water. m.p.: 212° C.
$v_{max}^{nujol}$ (ck$^{-1}$): 3450, 3125, 1735, 1655, 1605

| Elemental analysis: | C (%) | H (%) | N (%) |
| --- | --- | --- | --- |
| Calculated for C$_{19}$H$_{15}$N$_3$O$_3$.0.3H$_2$O | 67.37 | 4.64 | 12.40 |
| Found | 67.48 | 4.51 | 12.41 |

EXAMPLE 17

Following a procedure similar to that of Example 1 but using 2.544 g of 4-carbamoylimidazolium-5-olate and 5.922 g of p-benzyloxybenzoyl chloride, there was obtained 5-carbamoyl-1H-imidazole-4-yl p-benzyloxybenzoate.

Crude material was recrystallized from dimethylsulfoxide and water. m.p.: 215°–218° C. (dec.)
$v_{max}^{nujol}$ (cm$^{-1}$): 1730, 1680

| Elemental analysis: | C (%) | H (%) | N (%) |
| --- | --- | --- | --- |
| Calculated for C$_{18}$H$_{15}$O$_4$N$_3$ | 64.09 | 4.48 | 12.46 |
| Found | 63.5 | 4.5 | 12.3 |

EXAMPLE 18

Following a procedure similar to that of Example 1 but using m-trifluoromethylbenzoyl chloride, there was obtained 5-carbamoyl-1H-imidazole-4-yl m-trifluoromethylbenzoate. m.p. 208°–211° C. (dec.)
$v_{max}^{nujol}$ (cm$^{-1}$): 1730, 1670

| Elemental analysis: | C (%) | H (%) | N (%) |
| --- | --- | --- | --- |
| Calculated for C$_{12}$H$_8$O$_3$N$_3$F$_3$ | 48.17 | 2.7 | 14.04 |
| Found | 48.0 | 2.9 | 14.0 |

EXAMPLE 19

Following a procedure similar to that of Example 1 but using p-N-benzyloxycarbonylaminobenzoyl chloride, there was obtained 5-carbamoyl-1H-imidazole-4-yl p-N-benzyloxycarbonylaminobenzoate. m.p.: 187°–190° C. (dec.)
$v_{max}^{nujol}$ (cm$^{-1}$): 1730, 1680, 1660

| Elemental analysis: | C (%) | H (%) | N (%) |
| --- | --- | --- | --- |
| Calculated for C$_{19}$H$_{16}$O$_5$N$_4$ | 59.99 | 4.24 | 14.73 |
| Found | 59.6 | 4.3 | 14.5 |

EXAMPLE 20

Following a procedure similar to that of Example 1 but using 1.41 g of 4-biphenylcarbonyl chloride, there was obtained 1.33 g of 5-carbamoyl-1H-imidazole-4-yl p-henylbenzoate. m.p.: 225° C. (char.)

Crude material was recrystallized from N,N-dimethylformamide and water. m.p.: 226.5°–227° C. (char.)
$v_{max}^{nujol}$ (cm$^{-1}$): 3460, 3160, 1735, 1675, 1605

| Elemental analysis: | C (%) | H (%) | N (%) |
| --- | --- | --- | --- |
| Calculated for C$_{17}$H$_{13}$N$_3$O$_3$ | 66.44 | 4.26 | 13.67 |
| Found | 66.6 | 4.3 | 13.5 |

EXAMPLE 21

Following a procedure similar to that of Example 8 but using 1.1 g of o-acetylsalicyloyl chloride, there was obtained 1.29 g of 5-carbamoyl-1H-imidazole-4-yl o-acetoxybenzoate. m.p.: 143°–145° C.
$v_{max}^{nujol}$ (cm$^{-1}$): 3430, 3190, 1755, 1670, 1605

EXAMPLE 22

To a stirred solution of 6.3 ml of N,N-dimethylformamide in 14 ml of acetonitrile was added slowly 0.45 ml of oxalyl chloride at −20° C. and the reaction mixture was heated up to room temperature. To the reaction mixture was added 1.33 g of o-benzyloxycarbonylbenzoic acid at −25° C. and the reaction mixture was heated up to room temperature. To the reaction mixture were added 0.636 g of 4-carbamoylimidazolium-5-olate and 2.5 ml of dry pyridine over an ice bath in N$_2$ atmosphere and stirring was continued for 30 minutes at room temperature.

To the residue was added 1.9 ml of triethylamine over an ice bath and separated precipitates were filtered off and the filtrate was concentrated under reduced pressure to give 0.78 g of 5-carbamoyl-1H-imidazole-4-yl o-benzyloxycarbonylbenzoate. m.p.: 122°–124° C.
$v_{max}^{nujol}$ (cm$^{-1}$): 3460, 3150, 1770, 1725, 1670, 1610

EXAMPLE 23

Following a procedure similar to that of Example 1 but using 1.19 g of p-methoxycarbonylbenzoyl chloride, there was obtained 1.4 g of 5-carbamoyl-1H-imidazole-4-yl p-methoxycarbonylbenzoate.

Crude material was recrystallized from dimethylsulfoxide and water. m.p.: 215° C. (dec.)
$v_{max}^{nujol}$ (cm$^{-1}$): 3475, 3440, 3180, 3120, 1750, 1735, 1680, 1605

| Elemental analysis: | C (%) | H (%) | N (%) |
|---|---|---|---|
| Calculated for C$_{13}$H$_{11}$N$_3$O$_5$ | 53.98 | 3.83 | 14.53 |
| Found | 53.44 | 3.80 | 14.46 |

According to the present invention, there are obtained, for example, the following compounds:
5-carbamoyl-1H-imidazole-4-yl p-aminocinnamate,
5-carbamoyl-1H-imidazole-4-yl p-hydroxycinnamate,
5-carbamoyl-1H-imidazole-4-yl o-carboxycinnamate,
5-carbamoyl-1H-imidazole-4-yl α-cyano-4'-hydroxycinnamate,
5-carbamoyl-1H-imidazole-4-yl 3',4'dichlorocinnamate,
5-carbamoyl-1H-imidazole-4-yl 3',4'-dimethoxycinnamate,
5carbamoyl-1H-imidazole-4-yl 3',4'-dimethylcinnamate,
5-carbamoyl-1H-imidazole-4-yl 4'-hydroxy-3'-methoxycinnamate,
5-carbamoyl-1H-imidazole-4-yl 3',4',5'-trimethoxycinnamate,
5-carbamoyl-1H-imidazole-4-yl 3',4'-dihydroxycinnamate,
5-carbamoyl-1H-imidazole-4-yl α-fluorocinnamate,
5-carbamoyl-1H-imidazole-4-yl 3',5'-dimethoxy-4'-hydroxycinnamate,
5-carbamoyl-1H-imidazole-4-yl α-methylcinnamate,
5-carbamoyl-1H-imidazole-4-yl p-octylcinnamate,
5-carbamoyl-1H-imidazole-4-yl p-dodecylcinnamate,
5-carbamoyl-1H-imidazole-4-yl p-docosylcinnamate,
5-carbamoyl-1H-imidazole-4-yl p-octyloxycinnamate,
5-carbamoyl-1H-imidazole-4-yl p-octadecyloxycinnamate,
5-carbamoyl-1H-imidazole-4-yl pentafluorobenzoate,
5-carbamoyl-1H-imidazole-4-yl 2',4'-dicarboxybenzoate,
5-carbamoyl-1H-imidazole-4-yl 3'-amino-4'-methylbenzoate,
5-carbamoyl-1H-imidazole-4-yl 3'-acetyloxy-4'-methylbenzoate,
5-carbamoyl-1H-imidazole-4-yl 2'benzyloxy-5'-methylthiobenzoate,
5-carbamoyl-1H-imidazole-4-yl 4'-methylsulfonyl-3'-nitrobenzoate,
5-carbamoyl-1H-imidazole-4-yl 4'-chloro-3'-sulfamoylbenzoate,
5-carbamoyl-1H-imidazole-4-yl 2'-hydroxy-5'-methylthiobenzoate,
5-carbamoyl-1H-imidazole-4-yl 5'-formyl-2'-hydroxybenzoate,
5-carbamoyl-1H-imidazole-4-yl 2'-hydroxy-5'-sulfobenzoate,
5-carbamoyl-1H-imidazole-4-yl 4'-diethylamino-2'-hydroxybenzoate,
5-carbamoyl-1H-imidazole-4-yl 4'-methyl-3'-octyloxybenzoate,
5-carbamoyl-1H-imidazole-4-yl 4'-methyl-3'-octodecyloxybenzoate,
5-carbamoyl-1H-imidazole-4-yl 3'-methoxy-4'-lauroyloxybenzoate,
5-carbamoyl-1H-imidazole-4-yl 3'-methoxy-4'-stearoyloxybenzoate,
5-carbamoyl-1H-imidazole-4-yl 4'-hexadecyl-2'-methylbenzoate,
5-carbamoyl-1H-imidazole-4-yl 2'-dodecyl-4'-methoxybenzoate,
5-carbamoyl-1H-imidazole-4-yl p-aminobenzoate,
5-carbamoyl-1H-imidazole-4-yl p-hydroxybenzoate,
5-carbamoyl-1H-imidazole-4-yl o-benzoylbenzoate,
5-carbamoyl-1H-imidazole-4-yl o-carboxybenzoate,
5-carbamoyl-1H-imidazole-4-yl o-phenoxybenzoate,
5-carbamoyl-1H-imidazole-4-yl p-formylbenzoate,
5-carbamoyl-1H-imidazole-4-yl p-acetylbenzoate,
5-carbamoyl-1H-imidazole-4yl p-carbamoylbenzoate,
5-carbamoyl-1H-imidazole-4-yl p-octanoylbenzoate,
5-carbamoyl-1H-imidazole-4-yl p-palmitoylbenzoate,
5-carbamoyl-1H-imidazole-4-yl p-octyloxycarbonylbenzoate,
5-carbamoyl-1H-imidazole-4-yl p-octadecyloxycarbonylbenzoate,
5-carbamoyl-1H-imidazole-4-yl p-octanoyloxybenzoate,
5-carbamoyl-1H-imidazole-4-yl p-palmitoyloxybenzoate.

What is claimed is:
1. A compound of the formula:

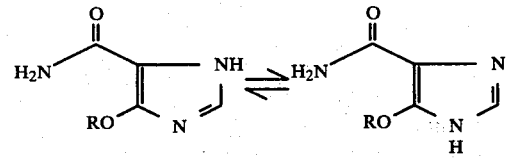

wherein R is cinnamoyl which is unsubstituted or substituted at its α position or phenyl ring with a member selected from the group consisting of alkyl, alkoxy, aryl, nitro, methylenedioxy, formyl, halogeno-alkyl, halogen, hydroxy, carboxyl, amino and cyano,
or a non-toxic salt thereof.

2. A compound according to claim 1, wherein said aryl is phenyl, tolyl or naphthyl.

3. A compound according to claim 1, wherein R is cinnamoyl.

4. A compound according to claim 1, wherein R is p-methylcinnamoyl.

5. A compound according to claim 1, wherein R is p-chlorocinnamoyl.

6. A compound according to claim 1, wherein R is 3,4-methylenedioxycinnamoyl.

7. A compound according to claim 1, wherein R is p-methoxycinnamoyl.

8. A compound according to claim 1, wherein R is p-formylcinnamoyl.

9. A compound according to claim 1, wherein R is m-trifluoromethylcinnamoyl.

10. A compound according to claim 1, wherein R is m-nitrocinnamoyl.

11. A compound according to claim 1, wherein R is α-phenylcinnamoyl.

* * * * *